United States Patent [19]

Kerby et al.

[11] Patent Number: 5,258,567

[45] Date of Patent: Nov. 2, 1993

[54] DEHYDROGENATION OF HYDROCARBONS

[75] Inventors: Michael C. Kerby; Kenneth L. Riley; Fred M. Long, all of Baton Rouge, La.; Jack W. Johnson, Clinton; John F. Brody, Bound Brook, both of N.J.

[73] Assignee: Exxon Research and Engineering Company, Florham Park, N.J.

[21] Appl. No.: 935,503

[22] Filed: Aug. 26, 1992

[51] Int. Cl.$^5$ .................. C07C 5/09; C07C 5/333
[52] U.S. Cl. ................... 585/654; 585/435; 585/440; 585/444; 585/658; 585/660
[58] Field of Search ............... 585/440, 654, 660, 442, 585/443, 444, 658

[56] References Cited

U.S. PATENT DOCUMENTS

| | | | |
|---|---|---|---|
| 4,791,088 | 12/1988 | Chu et al. | 502/232 |
| 4,952,544 | 8/1990 | McCauley | 502/68 |
| 5,063,039 | 11/1991 | Valyocsik | 423/329 |

Primary Examiner—Asok Pal
Assistant Examiner—P. Achutamurthy
Attorney, Agent, or Firm—Penny L. Prater; Henry E. Naylor

[57] ABSTRACT

This invention relates to a process for the dehydrogenation of $C_2$-$C_{10}$ hydrocarbons at dehydrogenation conditions with a pillared mica catalyst which contains an active metal selected from the group consisting of Pt, Cr and mixtures thereof, and a first modifier metal selected from the group consisting of Sn, Ga and mixtures thereof. The micas may also contain a second modifier metal selected from the group consisting of alkali metals, alkaline earth metals, and rare earth metals, and mixtures thereof.

19 Claims, No Drawings

DEHYDROGENATION OF HYDROCARBONS

FIELD OF THE INVENTION

This invention relates to a process for the dehydrogenation of hydrocarbons by contacting the hydrocarbons, at dehydrogenation conditions with a pillared mica catalyst which contains an active metal selected from the group consisting of Pt, Cr and mixtures thereof, and a first modifier metal selected from the group consisting of Sn, Ga and mixtures thereof. The micas may also contain a second modifier metal selected from the group consisting of alkali metals, alkaline earth metals, and rare earth metals, and mixtures thereof.

BACKGROUND OF THE INVENTION

Transportation fuels, particularly motor gasoline, contains a relatively high level of aromatic components, such as benzene. These fuels, while relatively high in octane number, are facing ever growing difficulty meeting ever stricter governmental environmental regulations with regard to emissions. This is primarily because of the high levels of aromatics. Consequently, there is much work being done to develop what has become known as "low emissions fuels". An important aspect of this work involves the substitution of non-aromatic components, having a relatively high octane value, for aromatic components of the fuel.

A class of non-aromatic components having relatively high octane value, which has been proposed for the production of low emissions fuels, are oxygenates. Non-limiting examples of preferred oxygenates for use in low emissions fuels include the unsymmetrical dialkyl ethers, particularly methyl tert-butyl ether (MTBE), ethyl tert-butyl ether (ETBE), and tert-amylmethyl ether (TAME). Conventional methods of manufacture of such ethers are typically based on liquid-phase reactions, such as the reaction of iso-butylene with methanol over cation-exchanged resins. This has created substantial demand for oxygenate building blocks, such as iso-butylene. Furthermore, other low carbon, or light, olefins are also in demand for the same reasons.

Low carbon number olefins, for example those having 2 to 10 carbon atoms, are typically obtained by the dehydrogenation of the corresponding paraffinic hydrocarbon. One method for light paraffin dehydrogenation is the so-called oxidative dehydrogenation process. In this process the light alkanes are reacted with oxygen over a suitably prepared mixed metal oxide catalyst to produce a mixture of olefin, water, $CO_x$, and unreacted paraffin. While high conversions combined with high olefin selectivities can be achieved, such a process has a number of disadvantages including loss of fuel value due to water and $CO_x$ formation. Furthermore, process operations are relatively costly and there are industrial hazards associated with exothermic combustion reactions.

A more direct and preferred approach is direct dehydrogenation over a suitable catalyst to produce olefins and molecular hydrogen. This chemistry has recently received considerable interest, although high reaction temperatures in the range of 500°–650° C. are required to obtain a significant equilibrium yield (e.g., 15–65%) of olefin. Moreover, under these reaction conditions, light alkane hydrogenolysis, for example to methane, is a competing and undesirable reaction. Most catalysts studied to date have not shown very high selectivities for dehydrogenation versus hydrogenolysis, or they have suffered from rapid catalyst deactivation necessitating frequent regeneration. As a consequence, process economics have not been favorable. Consequently, incentives exist for catalysts which: have high selectivity for the production of olefins; have improved resistance to deactivation; and can be regenerated using simple procedures, such as air treatment.

SUMMARY OF THE INVENTION

The present invention relates to a process for the dehydrogenation of hydrocarbons. The process comprises contacting a feedstream containing hydrocarbons selected from the group consisting of one or more $C_2$-$C_{10}$ non-aromatic hydrocarbon, and alkylated aromatic compounds wherein the alkyl group contains from about 2 to 10 carbon atoms; at dehydrogenation conditions; with a catalyst characterized as being a pillared mica comprising an active metal selected from the group consisting of Pt, Cr, Pd, Ir, Rd and mixtures thereof; and a modifier metal selected from the group consisting of Sn and Ga. The catalyst may further contain a second modifier metal selected from the group consisting of alkali metals (e.g., Na), alkaline earth metals (e.g., Mg, Ca) and rare earth elements (e.g., Nd, La, Ce).

In a preferred embodiment of the present invention about 0.05 to 2 wt. % of active metal is present and about 0.5 to 5 wt. % of a first modifier is present.

In another preferred embodiment of the present invention up to about 4 wt. % of a second modifier is present.

DETAILED DESCRIPTION OF INVENTION

Hydrocarbon streams which can be dehydrogenated using the pillared micas of the present invention are those streams containing predominantly $C_2$ to $C_{10}$ hydrocarbons. The preferred $C_2$ to $C_{10}$ hydrocarbons are alkanes; alkenes; alicyclic compounds, such as cyclohexane; alkylaryl compounds, wherein the alkyl group contains from about 2 to 10 carbon atoms, such as ethylbenzene; and naphthenoaromatics, such as tetrahydronaphthalene. Particularly preferred are $C_2$ to $C_6$ hydrocarbons, and more particularly preferred are $C_2$ to $C_5$ hydrocarbons, especially the alkanes, iso-butane and iso-pentane. It is to be understood that derivatives of the above hydrocarbons may also be used in the practice of the present invention, such as alcohols, halides, carboxylic acids, and the like. Typical hydrocarbon streams which will be treated in accordance with the present invention are petroleum refinery streams. Non-limiting examples of such streams are the $C_2$ to $C_6$ streams which result from reforming, coking, hydrocracking, distillation, and fluid catalytic cracking.

The catalyst of the present invention can be prepared from synthetic fluoromicas such as sodium tetrasilicic mica (NATSM) and synthetic taenionlite. Tetrasilicic micas may, in this application, also be described as tetrasilicic fluoromicas. Synthetic fluoromicas, such as sodium tetrasilicic mica ($Na[Mg_{2.5}Si_4O_{10}F_2]$), and lithium taeniolite ($Li[(Mg_2Li)Si_4O_{10}F_2]$) undergo swelling in water and other suitable polar solvents which enables the micas to be pillared. Even though fluoromicas such as these exhibit high layer charge densities they are capable of undergoing pillaring reactions with large cations. The resulting pillared tetrasilicic micas exhibit good thermal stability and are typically good catalysts for cracking, isomerization, etc.

The pillared micas used in the practice of the present invention possess an internal microstructure which may be established by introducing discrete, non-continuous inorganic oxide particles, or pillars, having a height between about 5 and 20 Å, preferably 6 to 18 Å, more preferably 6 to 16 Å, between the mica layers. The primary layers in 2:1 clay minerals are about 10 Å thick. Much work has been done to demonstrate that these platelets may be separated further by insertion of various polar molecules, such as water, ethylene glycol, various amines, etc., and that the platelets can be separated by as much as 30 to 40 Å. In the present invention, the pillars are preferably composed of alumina ($Al_2O_3$). These pillars serve to hold the space between the clay layers open after removal of occluded water and serve to form an internal interconnected micropore structure throughout the inner layer in which the majority of the pores are less than about 30 Å in diameter.

The micas used in the present invention may be produced by reacting the synthetic fluoromica with a polymeric cationic hydroxy multimetal complex. This complex may itself be produced by reacting a solution containing certain active metal-containing compounds with a polymeric cationic hydroxy complex solution. Preferred active metals are Pt, Pd, Cr, Ir, and Rh. More preferred is Pt, particularly the form of dihydrogen hexachloroplatinum. The cation of the complex is selected from aluminum, zirconium, and chromium. A preferred polymeric cationic hydroxy complex solution is an aluminum chlorohydroxide solution, such as "CHLORHYDROL MICRO-DRY", manufactured by Reheis Chemical Co. and containing about 23.5 wt. % $Al_2O_3$. Also suitable are any partially hydrolyzed alumina solutions containing aluminum polyoxocations. The solution may be heated to convert the hydrolyzed polymer complex into a polymeric cationic hydroxy multimetal complex. The polymeric cationic hydroxy multimetal complex may be, of course, produced by a variety of other ways, including introducing additional metals as modifiers into the initial cationic solutions used in the polymer synthesis. Such additional modifier metals may include a first modifier selected from Sn and Ga, and optionally a second modifier metal selected from the alkali, alkaline-earth, and rare earth metals.

In one embodiment of the present invention, the modified pillared micas incorporate an effective amount of a second modifier metal selected from alkali, alkaline earth, rare earth metals and mixtures thereof, in addition to the active metal and the first modifier metal. By the term "effective amount of modifier" is meant that concentration range of modifier which will improve the selectivity and reduce the cracking tendencies of the resulting micas when used for the dehydrogenation of $C_2$ to $C_{10}$, preferably $C_2$ to $C_5$, hydrocarbons. Suitable examples of modifiers include alkali metals such as Na and Li, preferably Na; alkaline earth metals such as Mg and Ca, preferably Mg; and rare earth metals such as Nd, La, Ce.

The active metal component, or mixtures thereof, may be present in the range of from about 0.05 to 2 wt. %, preferably 0.1 to 1.5 wt. % and more preferably from 0.15 to 1 wt. %. If both Sn and Ga are present as a first modifier metal, then the combined amount may be from about 0.05 to 5 wt. %. If Sn is present alone, the preferred amount is from about 0.1 to 1 wt. % and the most preferred amount is from about 0.15 to about 0.8 wt. %. If Ga is present alone, the preferred amount is from about 0.1 to 3 wt. % and the most preferred amount is from about 0.15 to about 2.5 wt. %. If a second modifier metal is used, the amount will range from about 0.1 to 2 wt. %, preferably from about 0.1 to 1 wt. %, and most preferably from about 0.2 to 0.6 wt. %. This is in addition to any native alkali or alkaline earth metals present in the unwashed mica.

Both the first and second modifier metals may be incorporated into the pillared micas by techniques such as by impregnation on the pillars prior to pilling and crushing of the finished catalyst. If impregnation is used, the pillared mica, in a dry or solvated state, is contacted, or otherwise incorporated with, a solution containing one or more of the modifier metals and thereby impregnated by the "incipient wetness" technique. Separate solutions can be used to incorporate each metal, or more than one metal can be incorporated with a single solution. This technique embodies absorption from a dilute or concentrated aqueous solution, with the total uptake of the metallic components being effected by filtration or evaporation. The solution used in impregnation can be a salt or acid solution having the respective modifier metal. Gallium nitrate is a convenient precursor for pillared mica modification, although other water and organic soluble compounds of Sn, Ga, or alkali, alkaline-earth, or rare earth metals may also be used. The impregnation treatment can be carried out under a wide range of conditions, including ambient as well as elevated temperatures. Atmospheric or superatmospheric pressures may be used. Such techniques are within the skill of those of the art and a more detailed description of such "incipient wetness" techniques is not necessary herein.

The conditions below represent general dehydrogenation conditions suitable for use with the micas of the present invention.

| Major Operating Variables | Typical Process Conditions | Preferred Process Conditions |
| --- | --- | --- |
| Pressure, psia | >0-50 | 1-20 |
| Reactor Temp., °C. | 400-650 | 500-625 |
| $H_2$/Alkane Molar Feed Ratio | 0-5 | 0-3 |
| Feed Rate, LHSV* | 0.5-7 | 1-3 |

*(liquid hourly space velocity = volume of liquid per volume of catalyst per hour)

The following examples are presented for illustrative purposes and are not to be taken as limiting in any way.

EXAMPLES

The pillared micas of the instant invention were prepared by the following procedure:

500 grams of tetrasilicic mica, designated as NA-T5 (DM Clean A) obtained from Showa Sangyo Co., Ltd., were dispersed in 20 liters of deionized water by mixing 5 batches of 100 grams of said mica in 4 liters of water and blending each batch for 4 minutes. Each batch of blended mica mix was then decanted into a glass reaction vessel. The pH of the mica mix was adjusted to 5.0 as it was stirred. The mixture was allowed to settle for 1 hour. The mica mix was then spray-dried at an inlet temperature of 230°-250° C., an outlet temperature of 120°-135° C. and a feed rate of 4-5 liters/hour.

152.5 grams of CHLORHYDROL MICRO-DRY aluminum chlorohydrate powder, which contains 47.2 wt. % $Al_2O_3$, was mixed into 125 grams of deionized water in a reaction flask fitted with a condenser. Dihydrogen hexachloro-platinum (e.g. 0.6 wt. % Pt) and/or alkali (e.g. sodium nitrate), alkaline earth (e.g. magnesium nitrate), rare earth (e.g. neodymium nitrate) salts were added to the CHLORHYDROL solution. The Pt- and/or Pt-alkali-, Pt-alkaline-, Pt-rare earth-CHLORHYDROL solutions were heated to 90° C. with stirring for 24 hours and cooled to room temperature (about 22° C.). 4.5 liters of deionized water was added to the cooled solutions with stirring. Stirring was continued for 1 hour. The solution was then allowed to stand overnight at room temperature, thereby forming a polymeric cationic hydroxy multimetal complex. The composition of the complex used in any given example herein is indicated in the tables to follow.

225.8 grams of the spray-dried mica were added to the Pt-and/or Pt-alkali-, Pt-alkaline earth-, Pt-rare earth-CHLORHYDROL solutions with stirring and were heated to 90° C. Heating continued overnight. The dispersion was cooled and filtered. The filter cake was dispersed in 25.0 liters deionized water and filtered. This process was repeated until the filtrate was substantially chloride-free. The filter cake was dried at 127° C. overnight. It was calcined in air for 2 hours at 200° C., heated to 400° C. at 50° C./minute and held at 400° C. for 2 hours. The calcined material was washed by dispersion in 50.0 liters deionized water and filtered. The wash was repeated twice reducing sodium levels to about 0.4% by weight. The material was dried overnight at 127° C. The calcination step was repeated. In a more preferred embodiment, the washing step was omitted and sodium levels were maintained at from about 1.2 to 1.4% by weight. $SnCl_2$ (e.g. 0.4 wt. % Sn) or $Ga(NO_3)_3$ (e.g. 2.5 wt. % Ga) was added to the Pt-, Pt-alkali-, Pt-alkaline, Pt-rare earth-aluminum tetrasilicic mica via incipient wetness techniques and dried at 100° C. overnight. The micas were pilled and crushed as 14/35 mesh particles. The surface area measured by the nitrogen BET method ranges from 220 to 340 $m^2/g$, and the layer repeat distance measured by X-ray powder diffraction was 18.2 to 18.8 Å.

The comparative clays were prepared by the following procedure:

277.5 grams of CHLORHYDROL 50% aluminum chlorohydrate solution (containing about 23.5% $Al_2O_3$, manufactured by Reheis Chemical Co.), was added to a reaction flask fitted with a condenser. This solution was then heated to 90° C. with stirring for 24 hours and was then allowed to cool to room temperature. 10.880 grams of AESAR dihydrogen hexachloroplatinum (IV) was then added. 4.5 liters of deionized water was added to the cool solutions with stirring. Stirring was continued for 2 hours. The solution was then allowed to stand overnight at room temperature, thereby forming a polymeric cationic hydroxy multimetal complex.

370.5 grams of VOLCLAY HPM-20, a technical grade microfine sodium bentonite clay obtained from the American Colloid Co., was added to the Pt-CHLORHYDROL solution with stirring and was heated to 90° C. Heating continued overnight. The resulting dispersion was cooled and filtered again. The filter cake was dispersed in 25.0 liters deionized water and filtered again. This process was repeated until the filtrate was substantially chloride-free. The filter cake was dried at 127° C. overnight. It was calcined in air for 2 hours at 200° C., heated at 400° C. at 50° C./minute and held for 2 hours. The calcined material was washed by dispersion in 50.0 liters deionized water and filtered. The wash was repeated twice. The calcined material was dried overnight at 127° C. The calcination step was repeated. $SnCl_2$ (e.g. 0.4 wt. % Sn) or $Ga(NO_3)_3$ (e.g. 2.5 wt. % Ga) was added to the Pt-, Pt-aluminum bentonite via incipient wetness techniques and dried at 100° C. overnight. The resulting clay micas were pilled and crushed as 14/35 mesh particles. They have a surface area of about 299 $m^2/g$, and a layer repeat distance of 18.8 Å.

I. Propane and Iso-Butane Dehydrogenation Procedure

A pillared mica sample (1.5 grams) was added to a quartz reactor tube and reduced under flowing $H_2$ (100 milliliters/minute) at 500° C. for 1 hour at 1 atmosphere. For propane dehydrogenation reactions, the temperature was raised to 605° C. and a mixture of hydrogen and propane at a molar ratio of 0.3 was passed over the mica sample at 1 atmosphere pressure. The products were constantly monitored using an on-line gas chromatography. Products were reported after 1 hour on stream. For iso-butane dehydrogenation reactions, the temperature was raised to 575° C. and a mixture of hydrogen and iso-butane/argon (11 vol. % iso-butane in argon) at a molar ratio of about 3.0 was passed over the mica at 1 atmosphere pressure. Products were reported after 10 hours on stream. This invention is illustrated by the following, nonlimiting examples.

EXAMPLE 1 (Comparative)

A 1.0% Pt by weight pillared mica (Mica A) was prepared as set forth above and washed after calcination. It was tested for propane and iso-butane dehydrogenation. The results are reported in Tables 1 and 2, respectively.

EXAMPLE 2

A 1.0% Pt by weight pillared mica (Mica B) containing 2.5 wt. % Ga was prepared as previously described and tested for propane and iso-butane dehydrogenation. The results are reported in Tables 1 and 2, respectively.

EXAMPLE 3

A 1.0% Pt by weight pillared mica containing 0.4 wt. % Sn (Mica C) was also prepared as set forth above and tested for propane and iso-butane dehydrogenation. The results are reported in Tables 1 and 2, respectively.

TABLE 1

RELATIVE PERFORMANCE OF MICAS FOR DEHYDROGENATION OF PROPANE

| Mica | Composition (wt. %) | Propane Conversion (wt. %) | Propylene Selectivity (wt. %) | Propane Yield (wt. %) |
|------|---------------------|---------------------------|-------------------------------|----------------------|
| A | 1 Pt–0.4 Na | 29 | 84 | 24 |
| B | 2.5 Ga/1 Pt–0.4 Na | 31 | 96 | 30 |
| C | 0.4 Sn/1 Pt–0.4 Na | 36 | 94 | 32 |

Reaction Conditions: 605° C.; 1 atmosphere; LHSV = 1; sample time 1 hour.

As shown in Table 1, the addition of 2.5 wt. % Ga (Mica B) and 0.4 wt. % Sn (Mica C) to the Pt pillared mica increased propane conversion and enhanced propylene selectivity. The bimetallic micas produce little hydrogenolysis (i.e. $C_1$–$C_2$) or oligomerization (i.e. $\geq C_4$) products.

TABLE 2

RELATIVE PERFORMANCE OF MICAS FOR DEHYDROGENATION OF ISO-BUTANE

| Composition | Iso-Butane Conversion | Iso-Butylene Selectivity | Iso-Butylene Yield |
|-------------|----------------------|--------------------------|--------------------|

TABLE 2-continued

| Mica | (wt. %) | (wt. %) | (wt. %) | (wt. %) |
|---|---|---|---|---|
| A | 1 Pt–0.4 Na | 33 | 71 | 23 |
| B | 2.5 Ga/1 Pt–0.4 Na | 46 | 90 | 41 |
| C | 0.4 Sn/1 Pt–0.4 Na | 48 | 81 | 39 |

Reaction Conditions: 575° C.; 1 atmosphere; LHSV = 1; sample time 10 hours

Table 2 demonstrates that the bimetallic mica catalysts, Pt-Ga (Mica B) and Pt-Sn (Mica C) show increased iso-butane conversions with concomitant increase in iso-butylene selectivities when compared with Mica A which contained only platinum.

EXAMPLE 4 (Comparative)

A 0.6% Pt by weight pillared mica (Mica D) was prepared and washed after calcination to reduce sodium content. Mica D was tested for iso-butane dehydrogenation. The results are reported in Table 3 below.

EXAMPLE 5

A 0.6% Pt by weight pillared mica (Mica E) containing 2.5 wt. % Ga was prepared. The mica was washed after calcination, providing a Na level of about 0.5% by weight. The mica was tested for iso-butane dehydrogenation, and the results are reported in Table 3 below.

EXAMPLE 6

A 0.6% Pt by weight pillared mica (Mica F) was prepared, containing 0.4 wt. % Sn and tested for iso-butane dehydrogenation. The mica was also washed after calcination, providing an Na level of about 0.5% by weight. The results are reported in Table 3 below.

TABLE 3
RELATIVE PERFORMANCE OF MICAS
FOR DEHYDROGENATION OF ISO-BUTANE

| Mica | Composition (wt. %) | Iso-Butane Conversion (wt. %) | Iso-Butylene Selectivity (wt. %) | Iso-Butylene Yield (wt. %) |
|---|---|---|---|---|
| D | 0.6 Pt–0.5 Na | 44 | 66 | 29 |
| E | 2.5 Ga/ 0.6 Pt–0.5 Na | 39 | 91 | 35 |
| F | 0.4 Sn/ 0.6 Pt–0.5 Na | 50 | 87 | 44 |

Reaction Conditions: 575° C.; 1 atmosphere; LHSV = 1; sample time 10 hours

As was observed for the 1% Pt by weight pillared mica, a 0.6% Pt by weight pillared mica also exhibits increased iso-butylene yields and selectivity with the addition of Ga (Mica E) or Sn (Mica F).

EXAMPLE 7

A 0.6% Pt by weight pillared mica (Mica G) was prepared but was not washed after calcination in order to maintain a sodium level of about 1.4% by weight. SnCl₂ (0.4 wt. % Sn) was added via wet impregnation techniques. Mica G was tested for iso-butane dehydrogenation, and the results are reported in Table 4 below.

EXAMPLE 8

A 0.6% Pt by weight pillared mica (Mica H) was prepared but was not washed after calcination in order to maintain a sodium level at about 1.4 wt. %. NaNO₃ (5 wt. % Na) and SnCl₂ (0.4 wt. %) was added via wet impregnation techniques. Mica H was tested for iso-butane dehydrogenation, and the results are reported in Table 4 below.

EXAMPLE 9

A 0.6% Pt by weight pillared mica (Mica I) was prepared but was not washed after calcination in order to maintain a sodium level of about 1.4% by weight. Mg(NO₃)₂ (0.5 wt. % Mg) and SnCl₂ (0.4 wt. % Sn) were added via wet impregnation techniques. Mica I was tested for iso-butane dehydrogenation, and the results are reported in Table 4 below.

TABLE 4
RELATIVE PERFORMANCE OF MICAS
FOR DEHYDROGENATION OF ISO-BUTANE

| Mica | Composition (wt. %) | Iso-Butane Conversion (wt. %) | Iso-Butylene Selectivity (wt. %) | Iso-Butylene Yield (wt. %) |
|---|---|---|---|---|
| F | 0.4 Sn/ 0.6 Pt–0.5 Na | 50 | 87 | 44 |
| G | 0.4 Sn/ 0.6 Pt–1.4 Na | 53 | 92 | 48 |
| H | 5 Na–0.4 Sn/ 0.6 Pt–1.4 Na | 27 | 94 | 26 |
| I | 0.5 Mg–0.4 Sn/ 0.6 Pt–1.4 Na | 60 | 94 | 57 |

Reaction Conditions: 575° C.; 1 atmosphere; LHSV = 1; sample time 10 hours

The above table shows that Pt-pillared micas which are not washed after the calcination step to maintain native sodium levels exhibit higher iso-butane conversions and iso-butylene selectivities (Mica G). However, excess amounts of sodium (>5 wt. %), while maintaining iso-butylene selectivity, decreases iso-butane conversion and iso-butylene yield (Mica H). The addition of an alkaline earth modifier further maximizes iso-butylene yields (Mica I compared to Mica G).

Table 5 below compares the performance of Mica I when used with a hydrogen co-feed, without a hydrogen co-feed, an at higher feed space velocities.

TABLE 5
RELATIVE PERFORMANCE OF MICAS
FOR DEHYDROGENATION OF ISO-BUTANE

| Mica | Composition (wt. %) | Iso-Butane Conversion (wt. %) | Iso-Butylene Selectivity (wt. %) | Iso-Butylene Yield (wt. %) |
|---|---|---|---|---|
| I | 0.5 Mg–0.4 Sn/ 0.6 Pt–1.4 Na | 60 | 94 | 57 |
| ¹I | 0.5 Mg–0.4 Sn/ 0.6 Pt–1.4 Na | 59 | 95 | 57 |
| ²I | 0.5 Mg–0.4 Sn/ 0.6 Pt–1.4 Na | 47 | 96 | 45 |

Reaction Conditions: 575° C.; 1 atmosphere; LHSV = 1; sample time 10 hours.
¹H₂/i-C4 = 0.
²LHSV = 3.

As shown in the above table, an alkaline modified Pt-Sn pillared mica exhibits similar iso-butylene yields without a hydrogen co-feed (catalyst ¹I). At higher feed space velocities, lower iso-butylene yields are produced (catalyst ²I).

EXAMPLE 10

A 0.6% Pt by weight pillared mica (Mica J) was prepared but was not washed in order to maintain a sodium level at about 1.4% by weight. Mg(NO₃)₂ (0.1 wt. % Mg) and SnCl₂ (0.4 wt. % Sn) were added via wet impregnation techniques. Mica J was tested for iso-butane dehydrogenation, and the results are reported in Table 6 below.

EXAMPLE 11

A 0.6% Pt by weight pillared mica (Mica K) was prepared but was not washed in order to maintain a sodium level at about 1.4% by weight. Mg(NO$_3$)$_2$ (1 wt. % Mg) and SnCl$_2$ (0.4 wt. % Sn) were added via wet impregnation techniques. Mica K was tested for iso-butane dehydrogenation, and the results are reported in Table 6 below.

TABLE 6
RELATIVE PERFORMANCE OF MICAS FOR DEHYDROGENATION OF ISO-BUTANE

| Mica | Composition (wt. %) | Iso-Butane Conversion (wt. %) | Iso-Butylene Selectivity (wt. %) | Iso-Butylene Yield (wt. %) |
|---|---|---|---|---|
| I | 0.5 Mg–0.4 Sn/ 0.6 Pt–1.4 Na | 60 | 94 | 57 |
| J | 0.1 Mg–0.4 Sn/ 0.6 Pt–1.4 Na | 50 | 86 | 43 |
| K | 1 Mg–0.4 Sn/ 0.6 Pt–1.4 Na | 40 | 95 | 38 |

Reaction Conditions: 575° C.; 1 atmosphere; LHSV = 1; sample time 10 hours

The above table shows that iso-butylene yields are maximized with a 0.5 wt. % Mg modifier (Mica I). Lower (Mica J) or higher (Mica K) Mg loadings decrease iso-butylene yields.

EXAMPLE 12

A 0.6% Pt by weight pillared mica (Mica L) was prepared but was not washed in order to maintain a sodium level at about 1.4% by weight. NaOH (0.5% Na) and SnCl$_2$ (0.4% Sn) were added via wet impregnation techniques. Mica L was tested for iso-butane dehydrogenation, and the results are reported in Table 7 below.

EXAMPLE 13

A 0.6% Pt by weight pillared mica (Mica M) was prepared but was not washed in order to maintain a sodium level at about 1.4 wt. %. Ca(NO$_3$)$_2$ (0.5 wt. % Ca) and SnCl$_2$ (0.4 wt. % Sn) were added via wet impregnation techniques. Mica M was tested for iso-butane dehydrogenation, and the results are reported in Table 7 below.

EXAMPLE 14

A 0.6% Pt by weight pillared mica (Mica N) was prepared but was not washed in order to maintain a sodium level at about 1.4 wt. %. Nd(NO$_3$)$_3$ (0.5 wt. % Nd) and SnCl$_2$ (0.4 wt. % Sn) were added via wet impregnation techniques. Mica N was tested for isobutane dehydrogenation, and the results are reported in Table 7 below.

TABLE 7
RELATIVE PERFORMANCE OF MICAS FOR DEHYDROGENATION OF ISO-BUTANE

| Mica | Composition (wt. %) | Iso-Butane Conversion (wt. %) | Iso-Butylene Selectivity (wt. %) | Iso-Butylene Yield (wt. %) |
|---|---|---|---|---|
| I | 0.5 Mg–0.4 Sn/ 0.6 Pt–1.2 Na | 60 | 94 | 57 |
| L | 0.5 Na–0.4 Sn/ 0.6 Pt–1.2 Na | 54 | 94 | 51 |
| M | 0.5 Ca–0.4 Sn/ 0.6 Pt–1.2 Na | 38 | 95 | 36 |
| N | 0.5 Nd–0.4 Sn/ 0.6 Pt–1.2 Na | 35 | 93 | 33 |

Reaction Conditions: 575° C.; 1 atmosphere; LHSV = 1; sample time 10 hours.

The above table shows that magnesium and sodium modifiers (Mica I and L) produce greater iso-butylene yields compared to either a calcium (Mica M) or a neodymium (Mica N) modifier. High iso-butylene selectivities (>93%) are maintained in all cases.

EXAMPLE 15

A 0.6% Pt–0.5% Nd pillared mica (Mica O) was prepared from a ND-CHLORHYDROL solution as set forth above but was not washed in order to maintain a sodium level at about 1.4 wt. %. SnCl$_2$ (0.4 wt. % Sn) was added via wet impregnation techniques. Mica O, the resulting mica, was tested for iso-butane dehydrogenation, and the results are reported in Table 8 below.

TABLE 8
RELATIVE PERFORMANCE OF MICAS FOR DEHYDROGENATION OF ISO-BUTANE

| Mica | Composition (wt. %) | Iso-Butane Conversion (wt. %) | Iso-Butylene Selectivity (wt. %) | Iso-Butylene Yield (wt. %) |
|---|---|---|---|---|
| N | 0.5 Nd–0.4 Sn/ 0.6 Pt–1.2 Na | 35 | 93 | 33 |
| O | 0.4 Sn/0.5 Nd– 0.6 Pt–1.2 Na | 58 | 91 | 53 |

Reaction Conditions: 575° C.; 1 atmosphere; LHSV = 1; sample time 10 hours.

The above table shows that iso-butylene yields are maximized when the rare earth modifier is added with the PT-CHLORHYDROL solution prior to the pillaring step (Mica O) rather than added to the pillared mica via wet impregnation techniques (Mica N).

EXAMPLE 16 (Comparative)

A 0.6% Pt by weight pillared bentonite clay (Clay 1) was prepared as set forth above and was tested for iso-butane dehydrogenation. The results are reported in Table 9 below.

EXAMPLE 17 (Comparative)

SnCl$_2$ (0.4 wt. % Sn) was added to a 0.6% Pt by weight pillared bentonite clay via wet impregnation techniques. The resulting clay (Clay 2) was tested for iso-butane dehydrogenation, and the results are reported in Table 9 below.

EXAMPLE 18 (Comparative)

NaNO$_3$ (1.2 wt. % Na) and SnCl$_2$ (0.4 wt. % Sn) were added to a 0.6% Pt by weight pillared bentonite clay via wet impregnation techniques. The resulting clay (Clay 3) was tested for iso-butane dehydrogenation. The results are reported in Table 9 below.

TABLE 9
RELATIVE PERFORMANCE OF MICAS FOR DEHYDROGENATION OF ISO-BUTANE

| Mica | Composition (wt. %) | Iso-Butane Conversion (wt. %) | Iso-Butylene Selectivity (wt. %) | Iso-Butane Yield (wt. %) |
|---|---|---|---|---|
| O | 0.6 Pt–0.5 Na | 44 | 66 | 29 |

TABLE 9-continued

RELATIVE PERFORMANCE OF MICAS
FOR DEHYDROGENATION OF ISO-BUTANE

| Mica | Composition (wt. %) | Iso-Butane Conversion (wt. %) | Iso-Butylene Selectivity (wt. %) | Iso-Butane Yield (wt. %) |
|---|---|---|---|---|
| Clay 1 | 0.6 Pt–0.1 Na | 11 | 82 | 9 |
| Clay 2 | 0.4 Sn/ 0.6 Pt–0.1 Na | 6 | 83 | 5 |
| Clay 3 | 1.4 Na–0.4 Sn/ 0.6 Pt–0.1 Na | 2 | 82 | 1 |
| G | 0.4 Sn/ 0.6 Pt–1.4 Na | 53 | 92 | 48 |

Reaction Conditions: 575° C.; 1 atmosphere; LHSV = 1; sample time 10 hours.

The above table shows that a Pt-pillared clay bentonite (Clay 1) is lower in dehydrogenation activity than a similar Pt-pillared mica (Mica O). Upon addition of Sn (Clay 2) or Sn and Na modifiers (Clay 3) a further reduction in activity is observed. This behavior is contrasted with the modified Pt-pillared mica (Mica G) which showed dehydrogenation activity and selectivity credits upon modification.

II. Regeneration of Dehydrogenation Micas Which Had Been Used as Catalysts

EXAMPLE 19

Regeneration for a 0.5 Mg-0.4 Sn/0.6 Pt-1.4 Na pillared mica (Mica I) employed a flow of air (100 milliliters/minute) for 2 hours at 550° C. Following a $N_2$ purge, the mica was reduced under a flow of $H_2$ (100 milliliters/minute) for 1 hour at 500° C. The dehydrogenation of iso-butane was carried out as described in earlier examples. The iso-butylene yield with two regeneration sequences after about 6, 10, 15 days on feed was obtained.

During the first yield period lasting 6.5 days, iso-butylene yields ranged from 53 to 40 wt. %. After a regeneration sequence described above, the second yield period lasting 3.75 days produced iso-butylene yields ranging from 51 to 43 wt. %. Following catalyst regeneration a third yield period lasting 4.5 days gave iso-butylene yields ranging from 52 to 43 wt. %. This example evidences the fact that the mica catalysts of the present invention can withstand a series of regenerations without a decrease in dehydrogenation activity.

What is claimed is:

1. A process for the dehydrogenation of hydrocarbons, which process comprises contacting a feedstream containing hydrocarbons selected from the group consisting of one or more $C_2$–$C_{10}$ non-aromatic hydrocarbons, and alkylated aromatic compounds wherein the alkyl group contains from about 2 to 10 carbon atoms; at dehydrogenation, conditions; with a catalyst characterized as being a pillared tetrasilicic fluoromica comprising an active metal selected from the group consisting of Pt, Cr, Pd, Ir, Rd and mixtures thereof; and a modifier metal selected from the group consisting of Sn and Ga.

2. The process of claim 1, wherein said fluoromica is further modified with a second metal selected from the group consisting of alkali metals, alkaline earth metals or rare earth metals and mixtures thereof.

3. The process of claim 1 wherein said pillars are substantially comprised of a metal oxide selected from the group consisting of alumina, zirconia, chromia or mixtures thereof.

4. The process of claim 3 wherein the pillars are comprised of alumina.

5. The process of claim 1, wherein said fluoromica contains from about 0.05 to 2 wt. % of an active metal or mixture of active metals.

6. The process of claim 5, wherein said fluoromica contains from about 0.1 to 1.5 wt. % of an active metal or mixture of active metals.

7. The process of claim 1, wherein said fluoromica contains from about 0.05 to 5 wt. % of a mixture of Sn and Ga.

8. The process of claim 1, wherein said fluoromica comprises from about 0.1 to 1 wt. % Sn and Ga is substantially absent.

9. The process of claim 1, wherein said fluoromica comprises from about 0.15 to 0.8 wt. % Sn and Ga is substantially absent.

10. The process of claim 1, wherein said fluoromica comprises from about 0.1 to 3 wt. % Ga and Sn is substantially absent.

11. The process of claim 1, wherein said fluoromica comprises from about 0.15 to 2.5 wt. % Ga and Sn is substantially absent.

12. The process of claim 2 wherein said fluoromica comprises from about 0.1 to 2 wt. % of modifiers selected from the group consisting of alkali, alkaline or rare earth elements.

13. The process of claim 12 wherein said fluoromica comprises from about 0.1 to 1 wt. % of modifiers selected from the group consisting of alkali, alkaline or rare earth elements.

14. The process of claim 2 wherein said modifiers are selected from the group consisting of Na, Mg, Ca, Nd, La and Ce.

15. The process of claim 1 wherein the dehydrogenation reaction is operated at a temperature from about 400° C. to 1200° C., and pressures from about 0.1 atmospheres to about 5 atmospheres.

16. The process of claim 15 wherein the dehydrogenation reaction is conducted in a reactor selected from a fluidized-bed reactor and a continuous moving-bed reactor.

17. The process of claim 1 wherein the feedstream is a $C_3$–$C_5$ refinery stream resulting from a petroleum refinery process.

18. The process of claim 6, wherein the hydrocarbon stream is a $C_3$–$C_5$ refinery stream resulting from a refinery process.

19. The process of claim 9, wherein the refinery process is selected from reforming, coking, hydrocracking, and fluid catalytic cracking.

* * * * *